United States Patent [19]

Maillefer

[11] Patent Number: 4,904,465
[45] Date of Patent: Feb. 27, 1990

[54] PERFUMING INGREDIENT, PROCESS FOR ITS PREPARATION AND UTILIZATION OF SAID INGREDIENT IN PERFUMING COMPOSITIONS AND PERFUMED PRODUCTS

[75] Inventor: Eric Maillefer, Echandens, Switzerland

[73] Assignee: Firmenich SA, Geneva, Switzerland

[21] Appl. No.: 310,565

[22] Filed: Feb. 15, 1989

[30] Foreign Application Priority Data

Feb. 25, 1988 [CH] Switzerland ............................ 701/88

[51] Int. Cl.$^4$ ........................... A61K 7/46; A61L 9/01
[52] U.S. Cl. ........................................ 424/70; 424/65; 424/76.2; 424/76.4; 512/23; 252/174.11
[58] Field of Search .................... 512/23; 424/70, 76.2, 424/76.4, 65; 252/174.11

[56] References Cited

PUBLICATIONS

Chemical Abstracts, vol. 83, 1975, p. 224, CA:62164d, Hydrogenation of Lignin Model Compounds in the Presence of a homogeneous Catalyst.
Chemical Abstracts, vol. 81, 1974, p. 103, CA:79577x, Hydrogenolysis of Lignin, V, Comparative Hydrogenation of 4-alkylsyringoles.
Chemical Abstracts, vol. 11, 1969, pp. 324–325, CA:90976r, Hydrogenolysis of Lignin, III, Comparative Hydration of 4-alkylphenols and 4-alkylguiacols.

*Primary Examiner*—Ellis P. Robinson
*Assistant Examiner*—Susan S. Rucker
*Attorney, Agent, or Firm*—Pennie & Edmonds

[57] ABSTRACT

New perfuming ingredient represented by the formula

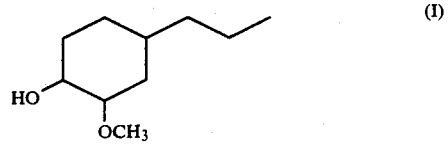

or 2-methoxy-4-propyl-1-cyclohexanol.

The compound possesses useful odor properties and can therefore be used advantageously for the preparation of perfuming compositions and perfumed products. The process for its preparation comprises the catalytic hydrogenation of eugenol.

5 Claims, No Drawings

PERFUMING INGREDIENT, PROCESS FOR ITS PREPARATION AND UTILIZATION OF SAID INGREDIENT IN PERFUMING COMPOSITIONS AND PERFUMED PRODUCTS

BRIEF SUMMARY OF THE INVENTION

The present invention relates to a method for enhancing, improving or modifying the odor properties of a perfuming composition or perfumed product, which method comprises adding to said composition or product a fragrance effective amount of 2-methoxy-4-propyl-1-cyclohexanol.

The invention also provides a perfuming composition containing as a perfuming ingredient 2-methoxy-4-propyl-1-cyclohexanol.

A further object of the invention is to provide a perfumed product containing as a perfuming ingredient 2-methoxy-4-propyl-1-cyclohexanol.

Finally, the instant invention further provides a process for the preparation of 2-methoxy-4-propyl-1-cyclohexanol which process comprises a catalytic hydrogenation of eugenol under a pressure of 100 to 300 bar and at a temperature of 75° to 200° C.

BACKGROUND OF THE INVENTION

The chemical structure of 2-methoxy-4-propyl-1-cyclohexanol, represented by the formula

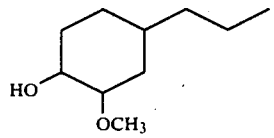

(I)

has been known for some time. The compound has in fact been described by S. W. Eachus and C. W. Dence [Holzforschung 29, 41-8 (1975)] as a product obtained by hydrogenation of isoeugenol, as part of a study related to the hydrogenation of compounds serving as lignin models. However, this reference is mute as to the fragrance properties of 2-methoxy-4-propyl-1-cyclohexanol.

PREFERRED EMBODIMENTS OF THE INVENTION

I have discovered that 2-methoxy-4-propyl-1-cyclohexanol possesses very interesting odor properties and that, as a result, it can be used advantageously as a perfuming ingredient for the preparation of perfume bases and concentrates, perfuming compositions and perfumed products.

The odor properties of this compound are such that it can be conveniently used to develop notes of the aromatic, green and natural type. Its scent is reminiscent of chervil, parsley, basil and artemisia. Since the notes it developes are of medium strength, it presents the advantage of being capable of combining with a great variety of commonly used perfuming coingredients, without disrupting the harmony of the composition to which it is added.

Owing to its odor characteristics, 2-methoxy-4-propyl-1-cyclohexanol can be used with equal advantage both in fine and in functional perfumery. This compound can thus be added to concentrated perfume compositions intended for alcoholic perfumery, concentrated perfumes or eaux de Cologne, or it can be used for perfuming a variety of products such as soaps, cosmetics, body milks or creams, and shampoos. Likewise, it can find use as a fragrance active ingredient in powder detergents or fabric softeners, air-fresheners or other materials, for instance plastic materials.

The proportions in which 2-methoxy-4-propyl-1-cyclohexanol can be employed to achieve the desired effects vary within a wide range of values. Thus, concentrations of the order of 0.5 to 1% by weight are perfectly convenient for the perfuming of materials such as soaps or detergents. On the other hand, concentrations of the order of 4 to 10%, or even higher, can be employed when 2-methoxy-4-propyl-1-cyclohexanol is used for the preparation of perfume compositions or concentrates.

Those skilled in the art will appreciate that such concentration values are only given as examples and that their evaluation depends on the nature of the products to be perfumed, of the coingredients present in a given composition and, naturally, on the specific fragrance effect that is desired to achieve. As coingredients, natural or synthetic compounds can be used. It would be quite superfluous to cite here the specific nature or number of these coingredients and the interested reader is referred to the works specialized in the art [see for example: S. Arctander, Perfume and Flavor Chemicals, Montclair, N.J. (1969)].

2-Methoxy-4-propyl-1-cyclohexanol can be prepared, as previously mentioned, by hydrogenation of isoeugenol according to the process described by Eachus and Dence. This compound can also be obtained by catalytic hydrogenation of eugenol using metallic catalysts such as palladium or ruthenium on alumina support, ruthenium on charcoal or Raney-nickel. The hydrogenation is carried out under pressure and, to this end, a pressure value between around 100 and 300 bar can be used. Temperatures of the order of 75° to 200° C. were used at these pressure values, and this made it possible to achieve conversion rates close to 100%, as well as excellent yields.

The reaction can be carried out using current equipment by means of a stainless steel autoclave. The thus obtained 2-methoxy-4-propyl-1-cyclohexanol can be purified, after separation of the reaction mixture, by the usual techniques, for example by fractional distillation.

The compound such as represented by formula (I) can define indifferently each of the isomers whose structure may be represented by one of the following formulae:

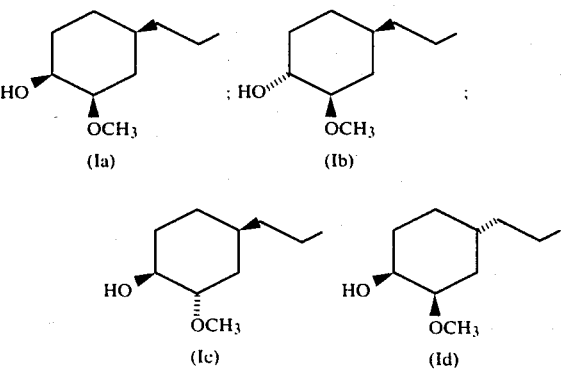

The various isomers can be separated, for example, by fractional distillation. Their specific characteristics will be discussed in detail in the examples which follow.

The respective ratio of these compounds in the obtained mixture is a function of the catalytic system used. Nevertheless, in all the cases studied, form (Ia) turned out to be preponderant.

The mixture of the various isomers is perfectly convenient for all the practical applications in perfumery. The various compounds can be used as isolated products if desired, after separation. Although their odor qualities are quite related, each isomer possesses characteristic properties. It was found in practice that compound (Ia) developed the most valued nuances. For practical and economic reasons, it is preferred to use the mixture as obtained by the process described above; however, reaction conditions can be chosen so as to obtain the product whose desired content in isomer (Ia) is the most favourable. To this end, the use of ruthenium on alumina is the most advantageous.

The invention will be illustrated in greater detail in the following examples wherein the temperatures are indicated in degrees centigrade and the abbreviations have the meaning common in the art.

EXAMPLE 1

Preparation of 2-methoxy-4-propyl-1-cyclohexanol 1000 g of eugenol and 10 g of 5% ruthenium on alumina in 800 g of ethanol were charged into a 5 l autoclave. After having purged the apparatus three times with a flow of nitrogen (2 kg/cm$^2$) and three times with hydrogen (2 kg/cm$^2$), the reaction mixture was heated to 85° under vigorous stirring. The evolution of the reaction was followed by successive chromatographic analyses and the reaction was carried out at 85° under a hydrogen pressure of 100 kg/cm$^2$. Once the hydrogenation was completed, the autoclave was depressurized and then purged with nitrogen. The product was then filtered and the catalyst recovered for subsequent use.

After evaporating the solvent, 1010 g of crude product were recovered, which, by fractional distillation on a filled column of 50 cm length, yielded, at 49°–55°/1.33×10$^2$ Pa, 910 g of the desired product (yield 86.8%). The product could then be separated in its isomeric components by means of a fractional distillation using a Normag type rotating band column of 1 m length and applying a vacuum of 1.33×10$^2$ Pa.

Four fractions were thus recovered.

| fraction | isomer | b.p. [°C.]/1.33 × 10$^2$ Pa |
|---|---|---|
| 1 | Ia | 43–45 |
| 2 | Id | 45–48 |
| 3 | Ib | 49–51 |
| 4 | Ic | 52–55 |

Ia or C-2-Methoxy-C-4-propyl-R-1-cyclohexanol $^1$H-NMR (360 MHZ): 4.1 (1H, m); 3.39 (3H, s); 3.15 (1H, m); 2.1 (1H, s); 1.97 (1H, m); 1.74 (1H, m); 1.4–1.2 (9H, m); 0.88 (3H, t) delta ppm; $^{13}$C-NMR: 81.20(d), 65.76(d), 55.75(q), 39.21(t), 35.83(d), 31.89(t), 29.96(t), 25.76(t), 20.00(t), 14.31(q) delta ppm;
MS: 113, 129, 71, 41.

Ib or T-2-Methoxy-T-4-propyl-R-1-cyclohexanol $^1$H-NMR (360 MHZ)+D$_2$O: 3.4 (3H, s); 3.37 (1H, m); 2.95 (1H, m); 2.12 (1H, m); 1.99 (1H, m); 1.72 (1H, m); 1.4–1.2 (6H, m); 0.95 (1H, m); 0.88 (3H, t); 0.80 (1H, m) delta ppm;
$^{13}$C-NMR: 84.86(d), 73.99(d), 56.36(q), 38.91(t), 35.80(d), 35.03(t), 31.62(t), 30.59(t), 21.20(t), 14.29(q) delta ppm;
MS: 113, 129, 71, 41.

Ic or T-2-Methoxy-C-4-propyl-R-1-cyclohexanol $^1$H-NMR (360 MHZ): 3.56 (1H, m); 3.35 (3H, s); 3.20 (1H, m); 2.31 (1H, s); 1.75 (3H, m); 1.6–1.2 (8H, m); 0.09 (3H, t) delta ppm;
$^{13}$C-NMR: 80.52(d), 71.16(d), 56.21(q), 36.07(t), 31.84(t), 31.61(t), 25.56(t), 26.72(t), 20.38(t), 14.08(q) delta ppm;
MS: 113, 129, 71, 41.

The purity of the Id fraction (lower than 30%) did not allow elaborate spectral analysis.

The four isomers mentioned above could equally be identified by gazchromatographic analysis of the reaction mixture obtained, by means of a 60 m SPWAX column; progr. 80°(5')–220°; 5°/min. The results obtained from the various hydrogenation tests are summarized in the following table:

TABLE

| | Catalyst | P [bar] | T [C.] | Yield [%] | Isomeric ratio | | | |
|---|---|---|---|---|---|---|---|---|
| | | | | | (Ia) | (Ib) | (Ic) | (Id) |
| 1 | Pd*/Al$_2$O$_3$ | 280 | 200 | 99 | 44.3 | 18.4 | 12.2 | 25.1 |
| 2 | Ru*/Al$_2$O$_3$ | 100 | 85 | 87 | 67.6 | 22.1 | 2.6 | 7.7 |
| 3 | Ru*/C | 180 | 170 | 72 | 66.1 | 20.4 | 2.8 | 10.7 |
| 4 | Ni/Raney | 215 | 150 | 54 | 52.9 | 24.9 | 7.0 | 15.2 |

*5%

EXAMPLE 2

Perfuming composition

A base perfuming composition was prepared by mixing the following ingredients (parts by weight):

| Hexylcinnamic aldehyde | 260 |
|---|---|
| Isononyl acetate | 120 |
| Synthetic bergamot | 120 |
| p-tert-Butylcyclohexyl acetate | 100 |
| Lilial (registered trademark)[1] | 80 |
| Tetrahydrolinalol | 60 |
| alpha-Terpineol | 40 |
| Benzyl salicylate | 40 |
| Hydrotropic alcohol | 40 |
| 10%* Dimethyl-cyclohexene-carbaldehyde | 30 |
| Mentha citrata essential oil | 20 |
| Lavender oil | 20 |
| Prasinate[2] | 10 |
| 50%* Verdanthiol[3] | 10 |
| 10%* Methyl-nonyl aldehyde | 10 |
| Total | 960 |

[1] L. Givaudan: p-tert-butyl-alpha-methyl hydrocinnamic aldehyde
[2] Firmenich SA; ethyl 2-acetyl-4-methyl-4-pentenoate
[3] L. Givaudan; Lilial-methylanthranilate
*in ethyl phthalate The addition of 4 g of 2-methoxy-4-propyl-1-cyclohexanol, obtained according to Example 1, to 96 g of the base composition thus prepared resulted in a novel composition whose green, aromatic character was much more pronounced and elegant. Furthermore, the new composition possessed a rounder character and better diffusion capability.

EXAMPLE 3

Perfuming composition

A base perfuming composition was prepared by mixing the following ingredients (parts by weight):

| | |
|---|---|
| Estragol | 350 |
| Linalol | 200 |
| Geraniol | 120 |
| 10%* Basilex[1] | 100 |
| Limonene | 60 |
| delta[3]-Carene | 40 |
| Eugenol | 20 |
| Methyleugenol | 10 |
| Isoeugenol | 10 |
| Anisic aldehyde | 10 |
| alpha-Pinene | 10 |
| Sweet fennel essential oil | 10 |
| Total | 940 |

*in ethyl phthalate
[1] Firmenich SA; 3-methyl-9-methylene-tricyclo[5.2.1.0$^{2,6}$]dec-3-en-8-exo-yl acetate 6 g of 2-methoxy-4-propyl-1-cyclohexanol were added to 94 g of the base composition thus prepared. As a result, the aromatic character of the base acquired a "basil" note while becoming more natural, fresh and sweet.

What I claim is:

1. A method for enhancing, improving or modifying the odor properties of a perfuming composition or perfumed product, which method comprises adding to said composition or product a fragrance effective amount of 2-methoxy-4-propyl-1-cyclohexanol.

2. A perfuming composition containing as a perfuming ingredient 2-methoxy-4-propyl-1-cyclohexanol.

3. A perfumed product containing as a perfuming ingredient 2-methoxy-4-propyl-1-cyclohexanol.

4. As a perfumed product according to claim 3, a detergent, a fabric softener, a soap or an air deodorizer.

5. As a perfumed product according to claim 3, a cosmetic preparation, a shampoo or a body deodorizer.

* * * * *